(12) United States Patent
Krasner

(10) Patent No.: US 7,448,871 B2
(45) Date of Patent: Nov. 11, 2008

(54) APPARATUS AND METHOD FOR STORING AND TRANSPORTING TEETH

(76) Inventor: Paul R. Krasner, 18 S. Roland St., Pottstown, PA (US) 19464

( * ) Notice: Subject to any disclaimer, the term of this patent is extended or adjusted under 35 U.S.C. 154(b) by 0 days.

(21) Appl. No.: 11/299,035

(22) Filed: Dec. 9, 2005

(65) Prior Publication Data
US 2007/0134624 A1  Jun. 14, 2007

(51) Int. Cl.
  A61C 5/00 (2006.01)
  A61B 19/02 (2006.01)
(52) U.S. Cl. .................................. 433/215; 206/63.5
(58) Field of Classification Search ............... 206/63.5, 206/44 R, 83, 485, 485.1, 565, 521.15; 433/215, 433/49; 99/440
See application file for complete search history.

(56) References Cited

U.S. PATENT DOCUMENTS

| | | | |
|---|---|---|---|
| 481,337 A * | 8/1892 | Warthen | ..................... 99/409 |
| 3,111,760 A | 11/1963 | Semmelman | |
| 4,689,014 A | 8/1987 | Krasner | |
| 4,694,956 A | 9/1987 | Sims | |
| 4,802,853 A | 2/1989 | Krasner | |
| 4,923,058 A | 5/1990 | Dennison | |
| 4,934,534 A * | 6/1990 | Wagner | ..................... 206/568 |
| 5,050,729 A | 9/1991 | Karbowniczak | |
| 5,303,819 A | 4/1994 | Goldberg | |
| 5,394,989 A | 3/1995 | Delson | |
| 5,913,859 A | 6/1999 | Shapira | |
| 6,082,531 A | 7/2000 | Hazenbos | |
| 6,767,740 B2 | 7/2004 | Sramek | |
| 2003/0103950 A1 | 6/2003 | Sharpe | |
| 2004/0058442 A1 | 3/2004 | Shi | |
| 2005/0106724 A1 | 5/2005 | Schierholz | |

* cited by examiner

Primary Examiner—John J Wilson
(74) Attorney, Agent, or Firm—William H. Eilberg

(57) ABSTRACT

A device for storing and transporting a tooth includes a basket having two halves, each half including at least one net. When the halves of the basket are in abutment, the nets together form one or more compartments capable of holding a tooth. The basket is inserted into a container holding a cell preserving solution. The container is then sealed, and can then be stored or transported. In the case where there are multiple nets in each half, the teeth are stored in multiple separate compartments, and do not impinge against each other, or against the walls of the container, during storage or transportation. The stored teeth can later be used to recover cells, including stem cells, for medical use.

4 Claims, 3 Drawing Sheets

APPARATUS AND METHOD FOR STORING AND TRANSPORTING TEETH

BACKGROUND OF THE INVENTION

This invention relates to the field of storing and transporting human teeth which have been extracted, avulsed, or exfoliated.

It has been proposed to harvest stem cells from human teeth, or from tissues surrounding human teeth, for later use in repair or regeneration of various tissues of the body. This concept is described in U.S. Pat. No. 6,767,740, the disclosure of which is incorporated by reference herein. The stem cells may be obtained from residual dental pulp found on the tooth. The tooth may be a deciduous tooth that is naturally exfoliated, or a tooth that has been extracted during a dental procedure. The tooth could also be one which has been avulsed, such as in an accident or fight.

The prior art includes devices for storing an exarticulated tooth, as exemplified by U.S. Pat. Nos. 4,689,014 and 4,802,853, the disclosures of which are incorporated by reference herein. The above-cited patents provide an apparatus for suspending a tooth in a net, within a solution especially designed for preserving dental tissues. Storing the tooth in this way improves the likelihood of successful reimplantation.

The present invention provides a method and apparatus which facilitates the storage and transportation-of one or more human teeth, in a manner such that stem cells, or other tissues, can be recovered from the teeth, and used for various purposes.

SUMMARY OF THE INVENTION

The present invention comprises an apparatus for storing and transporting a tooth, the apparatus including a basket having a top half and a bottom half, the top half having one or more nets, and the bottom half also having one or more nets. The nets are positioned such that when the top and bottom halves are brought into abutment, the nets of the top and bottom halves together form one or more complete compartments capable of storing a tooth. The halves of the basket are provided with an attachment means, such that the two halves can be snapped together so as to be handled as a single unit. The basket, when the two halves have been snapped together, is inserted within a container holding a solution capable of preserving dental tissues.

Both halves of the basket preferably include a handle, which facilitates removal of the basket from the container, and reinsertion of the basket into the container.

The basket preferably includes a disk having one or more openings, each opening corresponding to a net. The basket may be made of molded plastic, the plastic defining the disk as well as the nets.

The invention also includes the method of using the structure described above. A tooth is placed in one of the nets formed in a first half of the basket. The second half of the basket is then affixed to the first half. When the halves are affixed to each other, the net or nets of each half complement the net or nets of the other half, thereby forming one or more closed compartments, each capable of holding a tooth. The assembly comprising the complete basket is then inserted into a container which holds a cell preserving solution. The container can then be sealed, such as by screwing a lid onto the top of the container, and stored and/or transported.

When it is desired to have access to the tooth, such as at a laboratory or dental office, the halves of the basket, still comprising one unit, are removed from the container. The halves of the basket are then pulled apart, freeing the tooth. The tooth, or the tissues thereof, can then be used for various purposes.

The invention therefore has the primary object of providing an apparatus and method for storing and/or transporting a tooth, such that dental tissues associated with the tooth are preserved.

The invention has the further object of providing a convenient apparatus for storing and/or transporting a plurality of teeth, such that the teeth are held in separate compartments and do not impinge against each other and against the walls of a container.

The invention has the further object of facilitating the storage of dental material, including stem cells, for later use in regeneration of biological tissues.

The reader skilled in the art will recognize other objects and advantages of the present invention, from a reading of the following brief description of the drawings, the detailed description of the invention, and the appended claims.

DETAILED DESCRIPTION OF THE INVENTION

The present invention comprises a device for storing and transporting one or more teeth, the teeth being held in a basket, the basket being inserted within a container filled with a cell preserving solution.

The basket comprises two halves which fit together to form a single unit, the two halves constituting near mirror images of each other.

Each half of the basket comprises a disk which is preferably integrally formed with at least one, and preferably a plurality of nets. Preferably, the disk and the nets are formed of plastic, and the nets are relatively stiff. When the halves of the basket are placed in abutment, and the nets of each half are placed in registration with the nets of the other half, the nets form a plurality of closed compartments, each compartment being capable of holding a tooth and being distinct from the other compartments. Thus, a tooth inserted within one of the compartments will be held lightly but firmly therein. When the basket is placed in the container that holds the cell preserving fluid, the natural movement of the fluid washes off any loose debris that may be on the teeth. The cells on the teeth, including stem cells, are preserved by the fluid.

Figure 1:
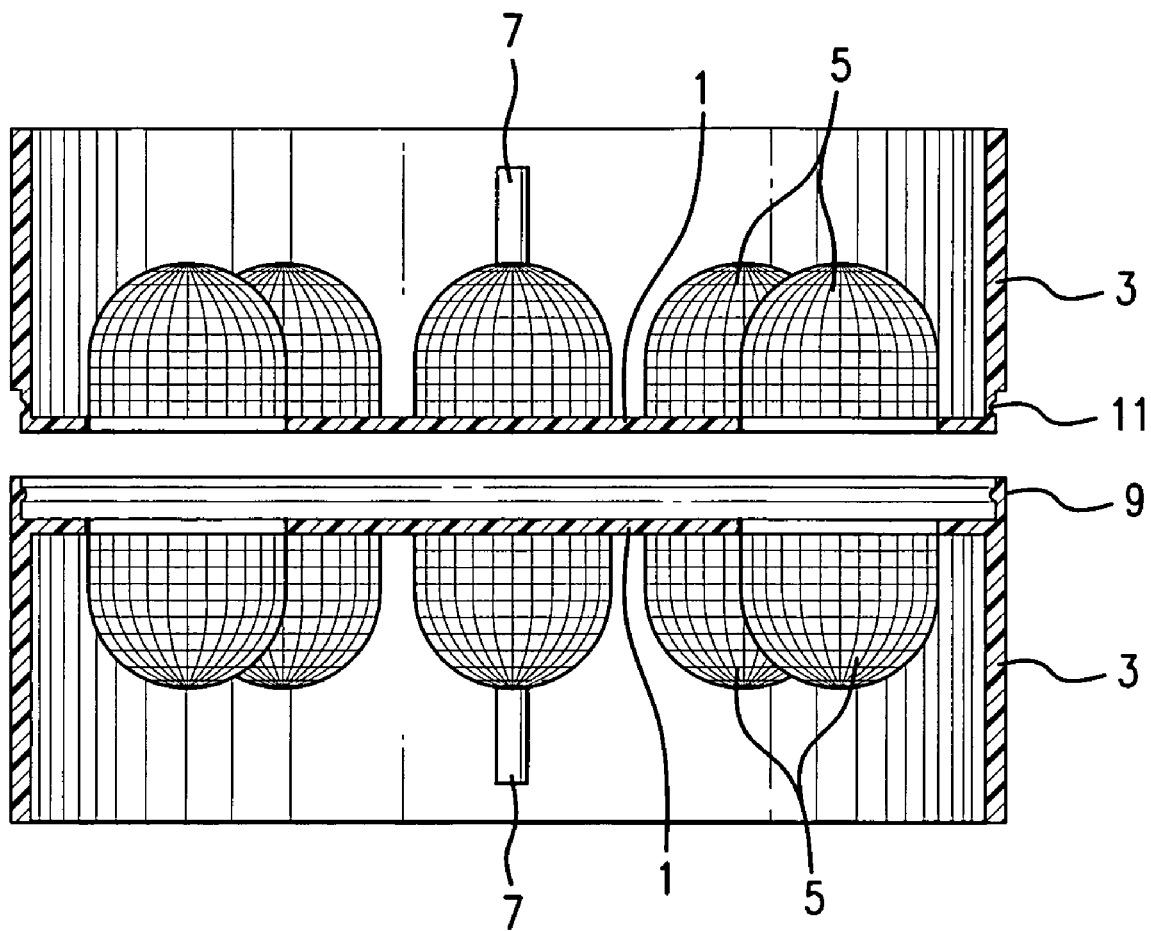
FIG. 1 provides an elevational view, partly in cross-section, of a two-piece, removable basket for storing teeth, made according to the present invention, the basket being shown with its two pieces having been separated.
Figure 2:
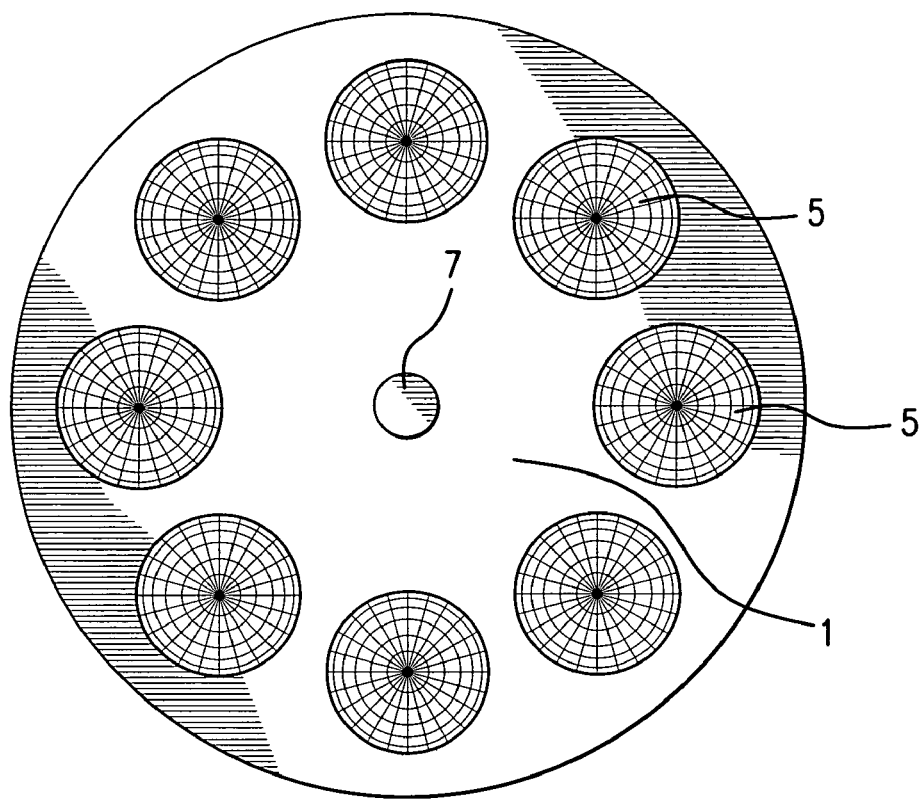
FIG. 2 provides a top view of one of the pieces of the basket for storing teeth, made according to the present invention.
Figure 3:
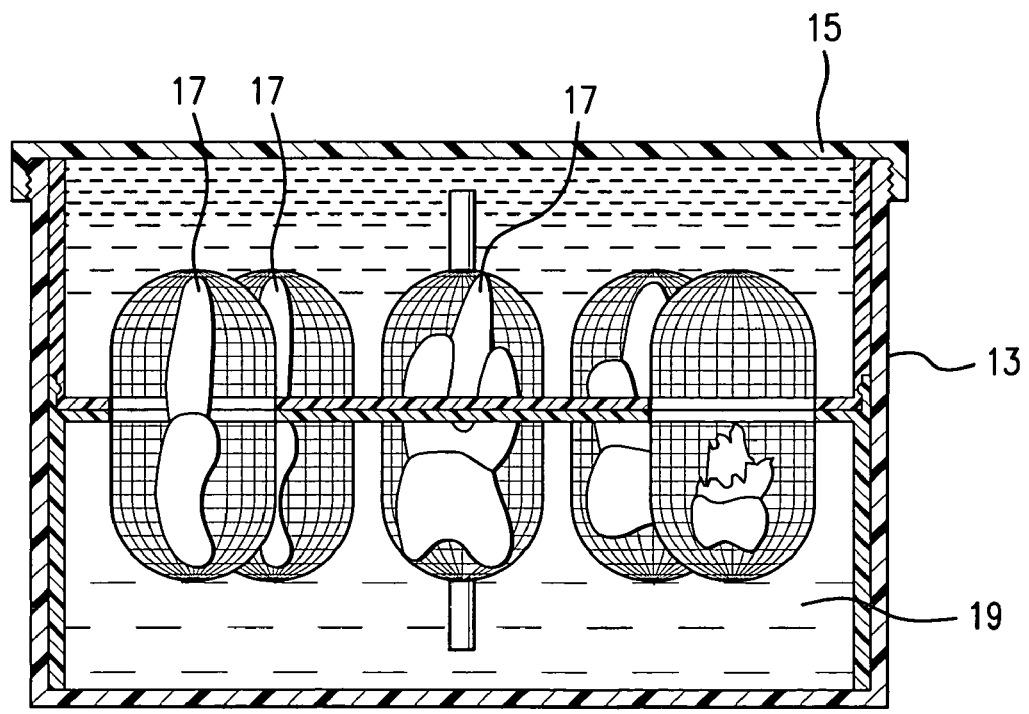
FIG. 3 provides an elevational view of the apparatus of the present invention, showing the removable basket held within a container.
Figure 4:
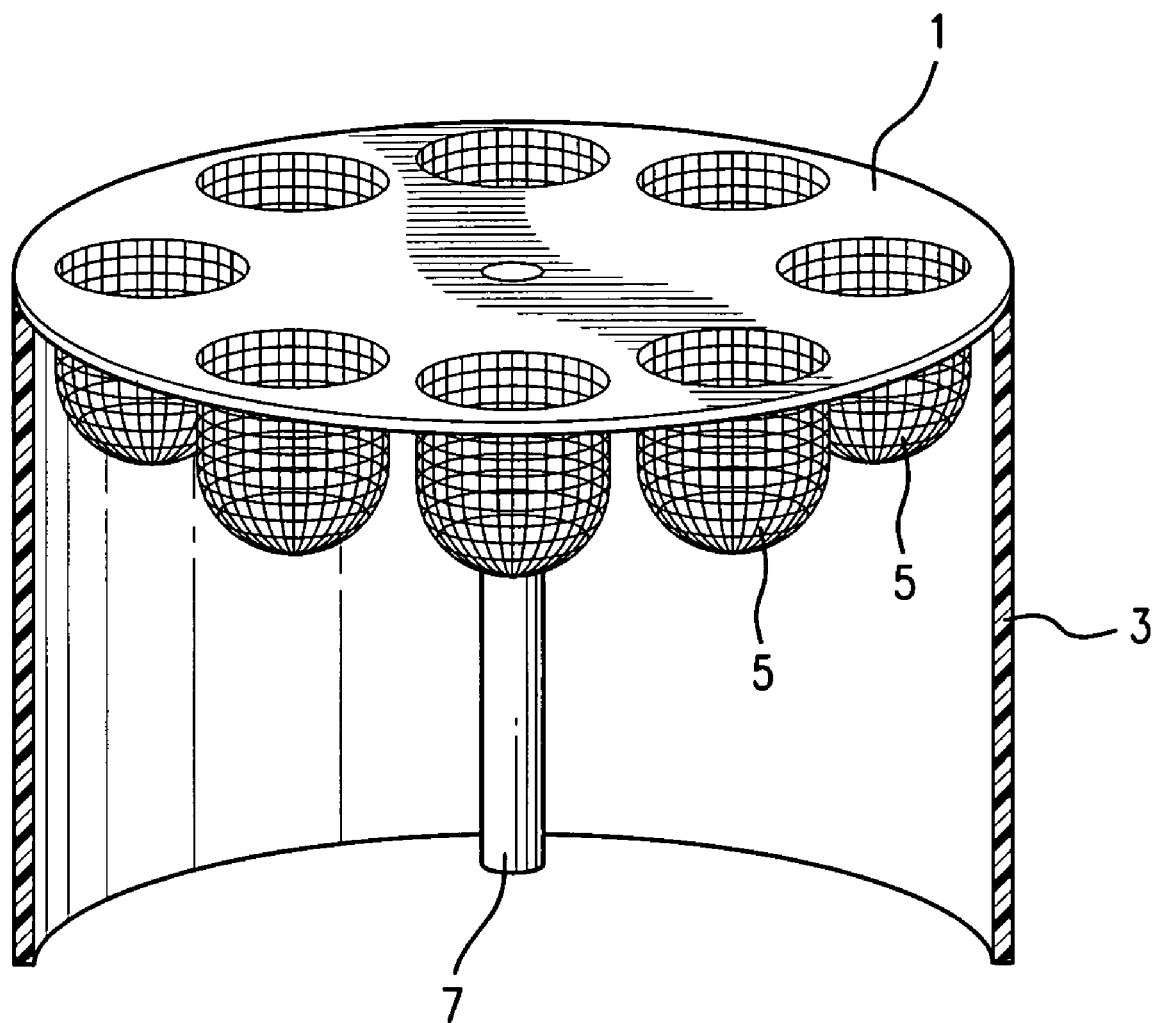
FIG. 4 provides a fragmentary perspective view showing one of the halves of the basket forming part of the present invention.

FIGS. 1 and 2 show the two-part basket of the present invention. FIG. 3 shows the assembled basket inserted within a container. FIG. 4 shows, in a fragmentary perspective form, one of the halves of the basket.

As shown, for example, in FIGS. 1 and 4, each half of the basket comprises a disk 1, a wall 3, and a plurality of nets 5 which are attached to the disk. The disk defines a plurality of openings, each opening corresponding with one of the nets. Preferably, the nets are molded integrally with the disk and the wall, so that the entire half-basket comprises one piece. However, the nets could be distinct from the disk and suitably joined thereto. The basket also includes handle 7, which is also preferably integrally formed with the disk. Alternatively, the handle could be separately formed and suitably joined to the disk.

In the preferred embodiment, the handle 7 comprises a rod which is attached to the disk. The handle could have other shapes, and it could be attached to the basket at other locations.

The lower half of the basket, as shown in FIG. 1, includes a flange 9 which mates with indentation 11 of the upper half of the basket, enabling the two halves to be snapped together, as shown in FIG. 3, to comprise one unit. The flange and indentation together comprise means for holding the two halves of the basket together. Other holding means could be provided instead of what is shown. The flange and indentations are positioned such that when the halves of the basket are brought into abutment, and the halves are about to be snapped together, the nets of one half are in registration with the nets of the other half, so that the nets form complete and distinct compartments for holding teeth.

FIG. 3 shows the entire device, including a container and the basket inserted therein. The container includes body 13 and lid 15. The lid is preferably screwed onto the body, as shown, though alternative means of attachment of the lid could be used instead. The lid comprises a seal for the container, substantially preventing contamination from the outside. In FIG. 3, the two halves of the basket have been snapped together to form a single unit. FIG. 3 illustrates the condition wherein the nets of both halves meet to form a plurality of closed, separate compartments, in which teeth 17 can be stored. The container is filled with a cell preserving solution 19.

As shown in the top view of FIG. 2, the nets are formed near a plurality of circular openings in the disk, the openings having diameters which are chosen so that the nets will not touch each other. That is, the openings are separated from each other, so that there is an appreciable amount of material between the openings. This arrangement insures that the disk is not unduly weakened structurally. Subject to this objective, the number of nets in the disk could be varied.

It is also possible to provide a single net for each disk. When the halves of the basket are brought into abutment, the nets would combine to form a single complete compartment, which could hold a single tooth or a plurality of teeth. The nets could be located virtually anywhere on the disks.

When it is desired to remove the basket from the container, one simply unscrews the lid, and removes the basket by grasping the handle that is nearest the upper portion of the container. Note that, in initially removing the basket, only the top handle is used, the bottom handle being inaccessible. But after the basket has been removed, the user may grasp the two handles and pull the halves of the basket apart. The use of two symmetric handles also has the advantage that the basket can be installed in either direction, while insuring that there will be a handle in the upper portion of the container.

The two halves of the basket are near mirror images of each other. The only departure from perfect symmetry, in the embodiment shown in the figures, is in the means of attachment of the two halves. In general, either half could be the top half and either half could be the bottom half.

The above-described device has several possible uses. First, it can be used to store and transport deciduous exfoliated teeth. Secondly, it can store and transport extracted wisdom teeth, or premolars extracted for orthodontic reasons. Thirdly, it can store and transport teeth which have been avulsed, such as in an accident or fight. The device can also store teeth which will be either immediately extracted and reimplanted, or transplanted to a different region of the mouth.

When any of the above needs arises, the tooth is placed in the described device. For example, if four wisdom teeth are extracted by an oral surgeon, he or she may place them into the bottom half nets of the device, with one tooth for each of four nets. The top half of the basket is then snapped onto the bottom half. The basket is immersed in the container, which bears a cell preserving solution, and the lid of the container is screwed on. The teeth will thus all be completely immersed in the cell preserving fluid, each within its own compartment. Even if the device is turned over, the nets will prevent the teeth from floating around and/or impinging against the sides of the container.

When the container arrives at its destination, the user, who may be a dentist or a laboratory technician, will unscrew the lid 15, and will remove the basket. The steps that follow depend on the nature of the teeth being stored and transported, as explained below.

1. Exfoliated Deciduous Teeth

The preferred sequence of steps is as follows. The user removes the top half of the basket, and then removes the deciduous tooth or teeth from the net(s), by grasping the tooth by the enamel. Next, the user may place the tooth in a special solution, which may be different from the solution in the container, the special solution being chosen such that it preserves stem cells. The user could use any available method to extract the stem cells from the tooth, and could then discard the tooth. The stem cells are then preferably preserved by cryogenic means, or by other means.

2. Extracted Wisdom Teeth

There are two possible techniques for handling an extracted wisdom tooth, or other extracted tooth.

In the first technique, the user removes the top half of the basket, and removes the wisdom tooth stored in the device. The entire tooth is then preserved, by cryogenic means, for possible later reimplantation.

In the second technique, applicable to cases where the patient has bone loss in the vicinity of the tooth, and wishes to grow the bone back, when the wisdom tooth is removed from the container, one scrapes off cells from the tip of the root of the tooth, and cryopreserves those cells. One could discard the tooth, or the tooth could also be cryopreserved for later use. This technique is appropriate where a patient has a tooth extracted for the sole purpose of harvesting stem cells for later treatment of a disease.

3. Avulsed Teeth

The user removes the basket from the container, and separates the halves of the basket. The user then removes the tooth from the basket, by grasping the tooth by the enamel portion of the crown. The tooth can then be reimplanted.

4. Intentional Reimplantation

In this technique, a dentist extracts a tooth, and places the tooth into the device of the present invention. The dentist cleans the abscess out of the socket, and treats the tooth root. The dentist then reimplants the tooth in its socket.

A preferred solution for preserving the tooth, in the device of the present invention, is a solution sold under the trademark VIASPAN, available from Barr Laboratories of Pomona, N.Y. Other solutions that could be used include those materials described in U.S. Pat. No. 4,689,014, cited above. Preferred solutions disclosed in the latter patent include the Hanks solution and Eagle's medium. The invention is not limited to use with the foregoing solutions, however.

The invention can be modified in various ways. The number of nets provided in the basket can be varied, as can the exact shape of the nets. The means for attaching the halves of the basket to each other can also be changed. The solution provided in the container can also be varied. These and other modifications, which will be apparent to the reader skilled in the art, should be considered within the spirit and scope of the following claims.

What is claimed is:

1. A method of storing and transporting a tooth, comprising:
   a) placing the tooth in a net, the net being attached to a first half of a basket,
   b) affixing a second half of a basket to said first half, wherein the second half also includes a net, such that nets of said first half and said second half together form a compartment enclosing the tooth, and
   c) inserting the first and second half baskets into a container holding a cell preserving solution.

2. The method of claim 1, further comprising sealing the container.

3. The method of claim 1, wherein the sealing step comprises screwing a lid onto the container.

4. The method of claim 1, further comprising unsealing the container, removing the halves of the basket from the container, and separating the halves of the basket so as to retrieve the tooth.

* * * * *